(12) United States Patent
Kamimura et al.

(10) Patent No.: US 11,543,576 B2
(45) Date of Patent: Jan. 3, 2023

(54) MEDICAL DISPLAY DEVICE

(71) Applicant: NIHON KOHDEN CORPORATION, Tokyo (JP)

(72) Inventors: Kazuya Kamimura, Tokorozawa (JP); Kazunori Yoshifuku, Tokorozawa (JP); Masaya Higuchi, Tokorozawa (JP); Takahiro Hasegawa, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 279 days.

(21) Appl. No.: 16/766,985

(22) PCT Filed: Nov. 19, 2018

(86) PCT No.: PCT/JP2018/042667
§ 371 (c)(1),
(2) Date: May 26, 2020

(87) PCT Pub. No.: WO2019/102963
PCT Pub. Date: May 31, 2019

(65) Prior Publication Data
US 2020/0315550 A1   Oct. 8, 2020

(30) Foreign Application Priority Data
Nov. 27, 2017   (JP) .............................. JP2017-226970

(51) Int. Cl.
*G02B 6/00* (2006.01)
*F21V 8/00* (2006.01)
*A61B 5/00* (2006.01)

(52) U.S. Cl.
CPC ............. *G02B 6/00* (2013.01); *G02B 6/0068* (2013.01); *A61B 5/743* (2013.01); *A61B 5/746* (2013.01); *A61B 5/7445* (2013.01)

(58) Field of Classification Search
CPC ...... G02B 6/00; G02B 6/0021; G02B 6/0053; G02B 6/0068; G02B 6/0073; G08C 19/16;
(Continued)

(56) References Cited

U.S. PATENT DOCUMENTS

2008/0203144 A1   8/2008   Kim
2011/0255303 A1*  10/2011  Nichol ................. G02B 6/0018
                                                     362/606
(Continued)

FOREIGN PATENT DOCUMENTS

| JP | 2011-072568 A | 4/2011 |
| WO | 2013-056160 A2 | 4/2013 |
| WO | 2013-173520 A2 | 11/2013 |

OTHER PUBLICATIONS

NPL Search {Apr. 27, 2022).*
(Continued)

*Primary Examiner* — Van T Trieu
(74) *Attorney, Agent, or Firm* — Pearne & Gordon LLP

(57) ABSTRACT

An alarm indicator (4) is provided with a light guiding member (41), a first light source (42) and a transmissive member (43). The light guiding member (41) extends in a first direction that is parallel to a display screen in which medical information is displayed. The first light source (42) faces an end face (41a) of the light guiding member (41) in the first direction. The transmissive member (43) covers the light guiding member (41) from a second direction intersecting with the first direction. The light guiding member (41) is provided with a light reflecting portion and an outer face (41d). The light reflecting portion extends in the first direction and reflects the light incident from the end face (41a) at least toward the second direction intersecting with the first direction. The light reflected by the reflecting
(Continued)

portion is emitted from the outer face (41*d*) while being diffused.

9 Claims, 4 Drawing Sheets

(58) Field of Classification Search
CPC ........ G06Q 30/00; G06Q 30/02; G06Q 50/06; G06D 50/00; G01N 21/88; G01N 21/8806; F21V 8/00
See application file for complete search history.

(56) References Cited

U.S. PATENT DOCUMENTS

| 2015/0117059 A1* | 4/2015 | Chun .................. | G02B 6/0045 |
| | | | 362/612 |
| 2015/0131309 A1* | 5/2015 | Umekawa ............ | G02B 6/0053 |
| | | | 362/606 |
| 2017/0140482 A1* | 5/2017 | Salter .................... | G08C 19/16 |

OTHER PUBLICATIONS

International Search Report Issued in Patent Application No. PCT/JP2018/042667 dated Jan. 23, 2019.
Written Opinion Issued in Patent Application No. PCT/JP2018/042667 dated Jan. 23, 2019.

* cited by examiner

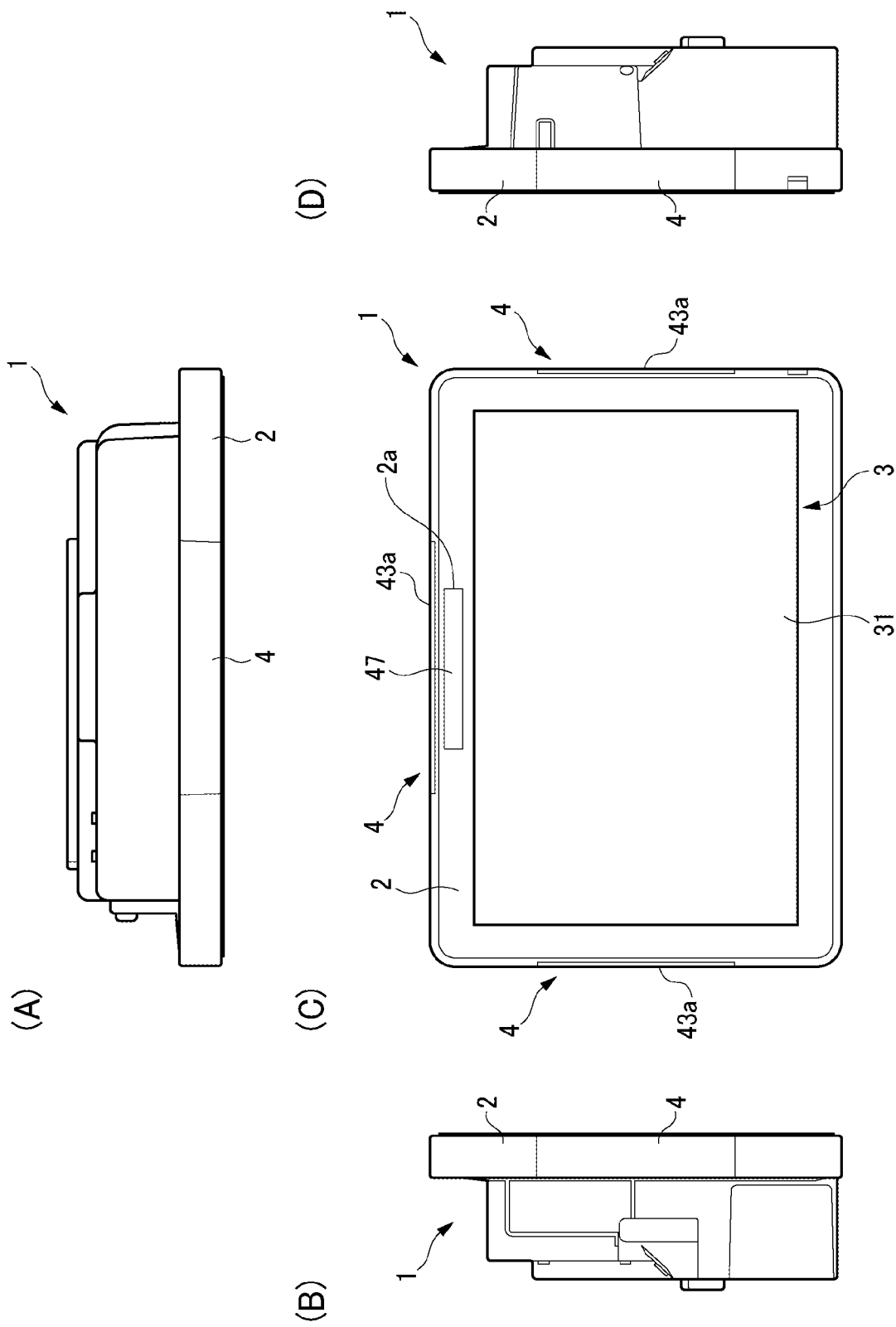

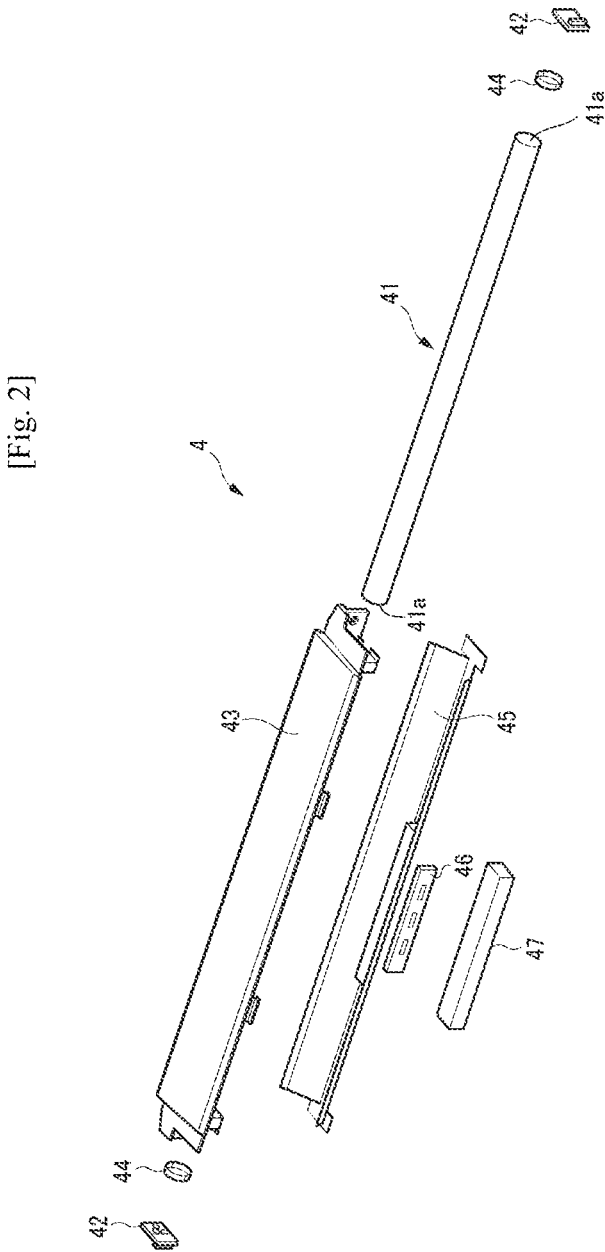
[Fig. 2]

[Fig. 3A]
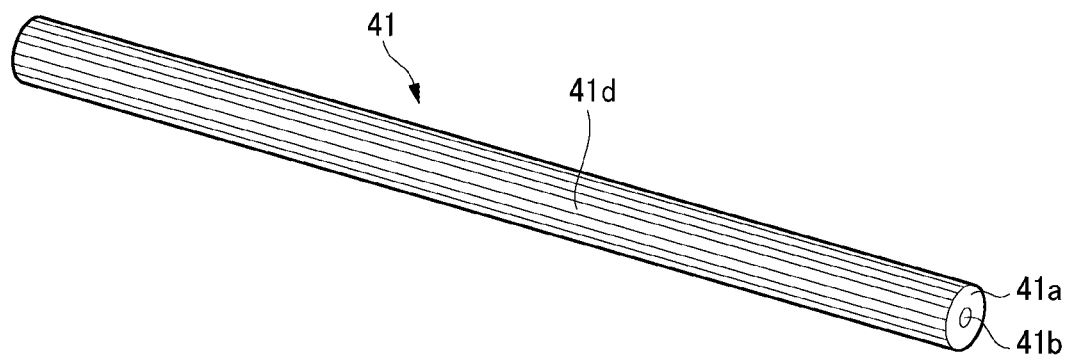
[Fig. 3B]
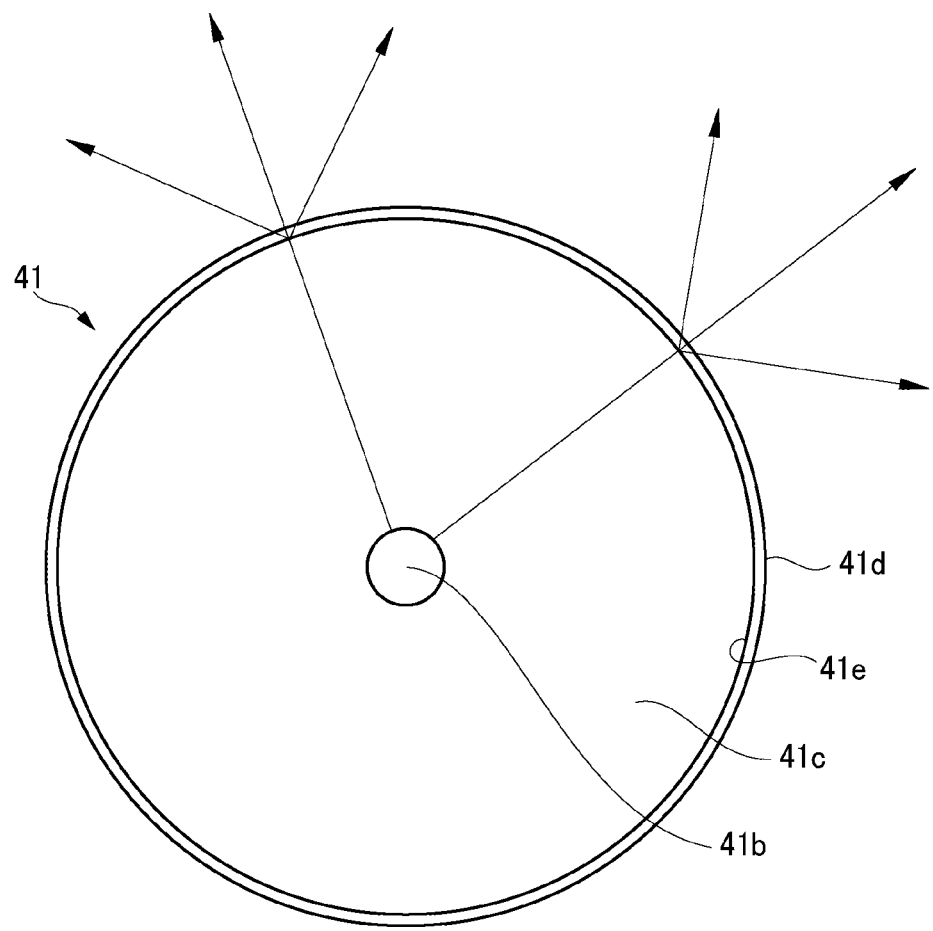

[Fig. 4A]
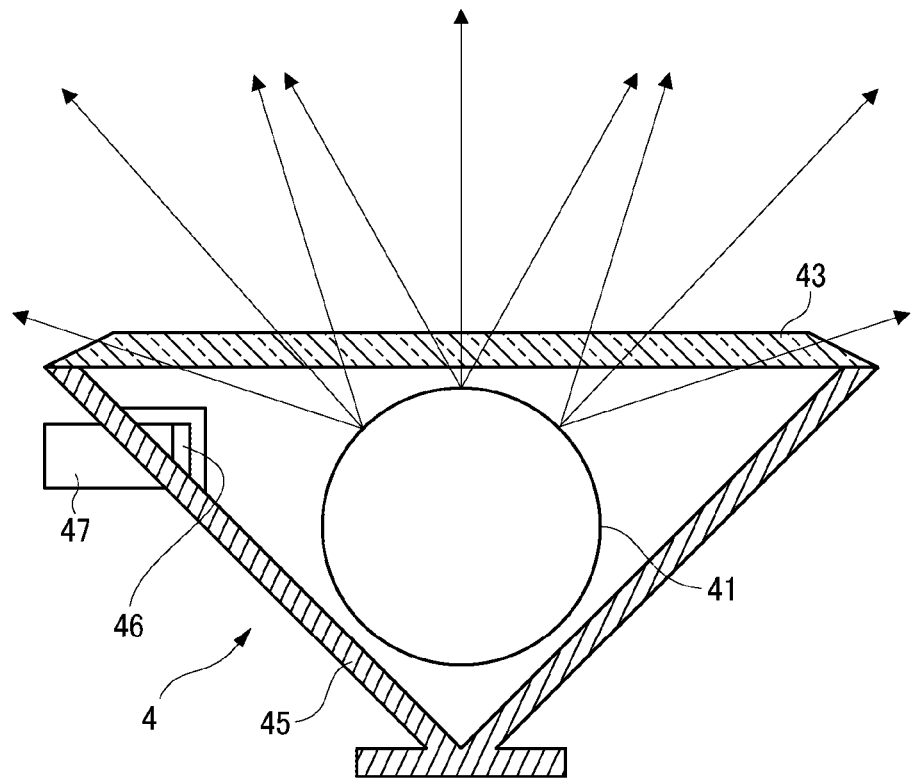
[Fig. 4B]
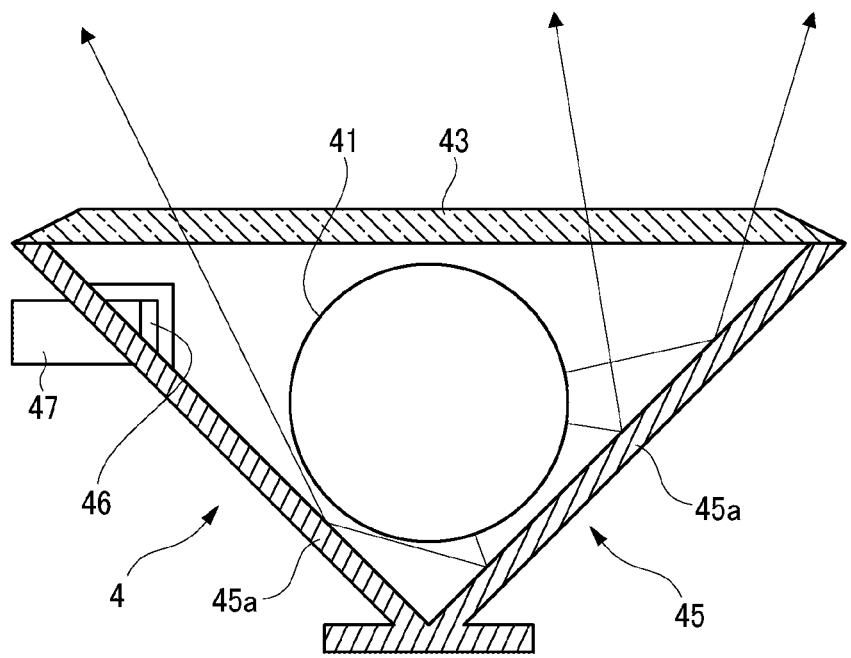

MEDICAL DISPLAY DEVICE

TECHNICAL FIELD

The presently disclosed subject matter relates to a medical display device.

BACKGROUND ART

Japanese Patent Publication No. 2011-072568A discloses a monitor device for vital signs information which is an example of a medical display device. The monitor device comprises an alarm indicator. The alarm indicator is disposed in an upper front portion of a housing of the monitor device. The alarm indicator is configured so as to light up or blink at a predetermined color in the case where, for example, the state of the biological information or the operation state of the device deviates from the normal state.

The user such as a medical person is not always in the vicinity of a monitor device or in front of an information displaying screen. In order to enable to promptly respond to, for example, a sudden change of the patient's condition, it is requested that the lighting or blinking of an alarm indicator can be seen from a place other than the vicinity of the monitor device or the front of the information displaying screen.

As countermeasures to satisfy the request, it is contemplated that the number of alarm indicators is increased to allow seeing from various directions. For example, it can be considered that, in addition to the above-described alarm indicator which is supposed to be seen mainly from the front side, another alarm indicator which is supposed to be seen mainly from the rear side is disposed. In this case, however, the number of light sources is increased, and therefore the enlargement of the structure, and the increase of the power consumption are inevitably caused.

SUMMARY OF THE INVENTION

The presently disclosed subject matter is intended to enable lighting and blinking of an alarm indicator to be seen from various places while avoiding the enlargement of the structure, and the increase of the power consumption.

An illustrative aspect of the presently disclosed subject matter provides a medical display device comprising:

an information displaying section having a display screen in which medical information is displayed; and an alarm indicator configured to provide alarm information, wherein the alarm indicator comprises:

a light guiding member extending in a first direction that is parallel to the display screen;

a first light source disposed so as to face an end face of the light guiding member in the first direction; and a transmissive member covering the light guiding member from a second direction intersecting with the first direction;

wherein the light guiding member comprises:

a reflecting portion extending in the first direction and configured to reflect light incident from the end face at least toward the second direction; and an outer face configured such that the light reflected by the reflecting portion is emitted therefrom while being diffused.

According to the above configuration, it is not necessary to prepare light sources that emit light respectively in various directions in which visibility is required. With the aid of the internal reflection and diffusion which are caused by the light guiding member, it is required a minimum number of first light source which causes light to be incident on the end face of the light guiding member in the longitudinal direction to obtain uniform emission light which propagates in various directions. Therefore, lighting and blinking of the alarm indicator are enabled to be visible from various places while suppressing the enlargement of the structure as well as the increase of the power consumption.

The term "transmissive" used herein means a capability of allowing light having a specific wavelength to pass through at least partially. That is, a transmissive member may be a transparent member or a translucent member.

BRIEF DESCRIPTION OF DRAWINGS

FIG. 1 illustrates external appearances of a monitor device according to one embodiment.

FIG. 2 illustrates elements constituting an alarm indicator of the monitor device.

FIG. 3A is a perspective view illustrating a light guiding member of the alarm indicator.

FIG. 3B is a section view illustrating the light guiding member.

FIG. 4A is a section view illustrating a portion of the alarm indicator.

FIG. 4B is a section view illustrating a portion of another alarm indicator.

DESCRIPTION OF EMBODIMENTS

Embodiments will be described below in detail with reference to the accompanying drawings. In FIG. 1, external appearances of a monitor device 1 for vital signs information according to one embodiment are illustrated. (A) is a top view. (B) is a left side view. (C) is a front view. (D) is a right side view.

The monitor device 1 is a device for continuously monitoring vital signs information which is acquired from a patient through at least one sensor that is not shown. Namely, the monitor device 1 is an example of the medical display device. The monitor device 1 comprises a housing 2, an information displaying section 3, and three alarm indicators 4.

The information displaying section 3 has a display screen 31. The display screen 31 is disposed on the front face of the housing 2. The above-described vital signs information is displayed on the display screen 31. The vital signs information is an example of medical information.

The alarm indicators 4 are disposed on upper, left side, and right side portions of the housing 2, respectively. The alarm indicators 4 light up or blink at a predetermined color to provide alarm information. The alarm information is information indicating that the state of the vital signs information, or the operation state of the monitor device 1 or the sensor deviates from the normal state.

In the case where the monitor device 1 is disposed in the bedside of a certain patient, the right-side and left-side alarm indicators 4 may be used for providing alarm information which is auxiliary with respect to that provided by the upper-side alarm indicator 4. When the upper-side alarm indicator 4 is to notify that the state of the vital signs information of the patient deviates from the normal state, for example, the right-side and left-side alarm indicators 4 can indicate the degree of the deviation by a difference in color or the like.

In the case where the monitor device 1 is disposed in the bedside of a certain patient, alternatively, the upper-side alarm indicator 4 may be used for providing alarm information relating to the patient, and the right-side and left-side alarm indicators 4 may be used for providing alarm information relating to other patients, respectively.

FIG. 2 is a perspective view illustrating elements constituting one of the alarm indicators 4. Among the three alarm indicators 4, the alarm indicator which is disposed in the upper portion of the housing 2 will be described.

The alarm indicator 4 comprises a light guiding member 41. The light guiding member 41 has a columnar shape which elongates in parallel with the display screen 31 of the information displaying section 3, and in the lateral direction of the housing 2. In other words, the longitudinal direction of the light guiding member 41 coincides with the lateral direction of the housing 2. The lateral direction of the housing 2 is an example of the first direction.

The alarm indicator 4 further comprises a pair of first light sources 42. The first light sources 42 are light-emitting elements which is able to emit light of at least one predetermined color. As the light-emitting elements, light-emitting diodes (LEDs), laser diodes (LDs), and organic EL (electroluminescence) elements may be exemplified. The first light sources 42 are disposed so as to face the end faces 41a in the longitudinal direction of the light guiding member 41, respectively. Namely, the light emitted from each of the first light sources enters of the light guiding member 41 from the corresponding end face 41a.

The alarm indicator 4 further comprises a transmissive member 43. The transmissive member 43 has a milky white appearance. For example, the transmissive member 43 is made of an acrylic resin or polycarbonate. The transmissive member 43 has transparency at least at the wavelength of the light which is emitted from the first light sources 42. The light guiding member 41 is covered by the transmissive member 43 from the upper side of the light guiding member 41. In other words, light guiding member 41 is covered by the transmissive member 43 from a direction intersecting with the longitudinal direction (the lateral direction of the housing 2) of the light guiding member 41. The direction directed from the upper side of the light guiding member 41 is an example of the second direction.

FIG. 3A is a perspective view illustrating the appearance of the light guiding member 41. FIG. 3B is a section view illustrating the light guiding member 41 as seen from a perpendicular direction of the longitudinal direction thereof. The section has a circular shape. FIG. 4A illustrates sections of the light guiding member 41 and the transmissive member 43, as seen from the longitudinal direction of the alarm indicator 4 illustrated in FIG. 2.

The light guiding member 41 comprises a reflecting portion 41b. The reflecting portion 41b is disposed so as to contain the central axis of the light guiding member 41 having a columnar shape. The reflecting portion 41b is configured so as to reflect the light incident from the end faces 41a in a direction intersecting with the longitudinal direction of the light guiding member 41.

The light guiding member 41 further comprises a light guiding portion 41c. The light guiding portion 41c is located outside the reflecting portion 41b in a direction intersecting with the longitudinal direction of the light guiding member 41. The light guiding portion 41c is a portion through which the light incident from the end faces 41a propagates.

The light guiding member 41 further comprises an outer face 41d. In the outer face 41d, surface treatment is performed such that at least part of the light which is reflected by the reflecting portion 41b is emitted while being diffused.

The light which is emitted from the first light sources 42 and incident from the end faces 41a has a direction component intersecting with the longitudinal direction of the light guiding member 41. Such light propagates in the light guiding portion 41c along the longitudinal direction of the light guiding member 41, while repeating total reflection from an inner face 41e as well as reflection from the reflecting portion 41b. The reflecting portion 41b and the light guiding portion 41c are made of an acrylic resin. The reflection from the reflecting portion 41b may be realized by differentiating the refractive indices of the reflecting portion 41b and the light guiding portion 41c from each other, or by forming a reflection layer made of a metal thin film or the like on the outer face of the reflecting portion 41b. Alternatively, the whole of the reflecting portion 41b may be formed by a metal.

Light having a direction component which does not undergo total reflection from the inner face 41e is emitted from the outer face 41d. At this time, the light is caused to propagate in various directions by the face treatment applied to the outer face 41d. As illustrated in FIG. 4A, the light emitted from the outer face 41d passes through the transmissive member 43, and is then directed to the outside of the monitor device 1. The light emitted from the first light sources 42 undergoes further diffusion by the transmissive member 43, and is visible from various directions (a range of about 180 degrees from the front to rear of the housing 2 as seen in the longitudinal direction of the alarm indicator 4).

According to the above configuration, it is not necessary to prepare light sources that emit light respectively in various directions in which visibility is required. With the aid of the internal reflection and diffusion which are caused by the light guiding member 41, it is required a minimum number of first light sources 42 which cause light to be incident on the end faces 41a of the light guiding member 41 in the longitudinal direction to obtain uniform emission light which propagates in various directions. Therefore, lighting and blinking of the alarm indicator 4 are enabled to be visible from various places while suppressing the enlargement of the structure as well as the increase of the power consumption.

The above description can be applied also to the two alarm indicators 4 which are disposed in the right-side and left-side of the housing 2, respectively. In this case, the light guiding members 41 elongate in parallel with the display screen 31 of the information displaying section 3, and in the vertical direction of the housing 2. The vertical direction of the housing 2 in this case is another example of the first direction. The transmissive members 43 cover the light guiding member 41 from the right-side and left sides of the housing 2, respectively. The lateral direction of the housing 2 in this case is another example of the second direction. The two alarm indicators 4 which are disposed in the right-side and left sides of the housing 2, respectively may be omitted in accordance with the specification of the monitor device 1.

As illustrated in FIG. 3B, the section of the reflecting portion 41b as seen in the longitudinal direction of the light guiding member 41 has a circular shape. Namely, the sectional shape of the reflecting portion 41b as seen in the longitudinal direction of the light guiding member 41 is similar to that of the whole light guiding member 41 as seen in the direction.

According to the above configuration, the directional dependency of the light emitted from the outer face 41d with a direction intersecting with the longitudinal direction of the light guiding member 41 is suppressed, and the light distribution can be easily controlled.

Namely, the sectional shape of the light guiding member 41 as seen in the longitudinal direction of the light guiding member 41 is not limited to a circular shape. An elliptic shape, a polygonal shape, or another shape can be adequately employed. In this case, it is preferable to make the sectional shape of the reflecting portion 41b as seen in the longitudinal direction of the light guiding member 41 similar to the shape which is adequately employed.

As illustrated in FIG. 3A, a plurality of fine grooves may be formed in the outer face 41d of the light guiding member 41. The grooves elongate in the longitudinal direction of the light guiding member 41. The grooves may be formed linearly as illustrated in the figure, or formed so as to spirally elongate in the longitudinal direction of the light guiding member 41.

According to the above configuration, the above-described light diffusion effect can be obtained by simple surface treatment.

The light diffusion effect is not necessarily obtained only by the plurality of grooves. The light diffusion effect can be obtained also by a plurality of fine ridges which are formed on the outer face 41d, and which elongate in the longitudinal direction of the light guiding member 41. Moreover, a configuration may be employed where the light diffusion effect is obtained by both a plurality of grooves and plurality of ridges which elongate in the longitudinal direction of the light guiding member 41.

As illustrated in FIG. 2, each of the alarm indicators 4 may comprise first reflecting members 44. In this case, each of the first reflecting members 44 is disposed between the light guiding member 41 and the corresponding first light source 42. The first reflecting members 44 are disposed so as to reflect part of the light emitted from the first light sources 42 and cause the reflected light to be incident on the end faces 41a of the light guiding member 41.

According to the above configuration, light emitted from the first light sources 42 in such directions that the light is not directly incident on the end faces 41a is enabled to be subjected to the above-described effect due to the light guiding member 41. Namely, the utilization efficiency of the light emitted from the first light sources 42 is enhanced, and the visibility of the light emitted from the alarm indicators 4 is improved.

As illustrated in FIG. 2, each of the alarm indicators 4 may comprise a second reflecting member 45. In this case, as illustrated in FIG. 4B, the second reflecting member 45 may have a pair of flat reflective faces 45a. The pair of reflective faces 45a are disposed so as to reflect the light emitted from the outer face 41d of the light guiding member 41, toward the transmissive member 43.

According to the above configuration, light that is emitted from the light guiding member 41 in such directions that the light is not directly incident on the transmissive member 43 can be directed toward the outside of the monitor device 1. Namely, the utilization efficiency of the light emitted from the first light sources 42 is enhanced, and the visibility of the light emitted from the alarm indicators 4 is improved.

As long as the light emitted from the outer face 41d of the light guiding member 41 can be reflected toward the transmissive member 43, the pair of flat reflective faces 45a may be redisposed with at least one curved reflective face.

As illustrated in FIG. 2, each of the alarm indicators 4 may comprise a second light source 46 and a transmissive member 47. In this case, the second light source 46 is a light-emitting element which is able to emit light of a predetermined color. As the light-emitting element, a light-emitting diode (LED), a laser diode (LD), and an organic EL (electroluminescence) element may be exemplified.

The transmissive member 47 has a milky white appearance. For example, the transmissive member 47 is made of an acrylic resin, polycarbonate, or silicone. The transmissive member 47 is disposed so as to face the second light source 46. The transmissive member 47 has transparency at least at the wavelength of the light which is emitted from the second light source 46. As illustrated in (C) of FIG. 1, an opening 2a may be formed in the front face of the housing 2. When the alarm indicator 4 is attached to the housing 2, the transmissive member 47 is disposed so as to be exposed through the opening 2a. Light emitted from the second light source 46 is guided to the front side of the housing 2 while being diffused by the transmissive member 47.

The second light source 46 may be fixed together with the transmissive member 47 to the side of the housing 2, or fixed to the second reflecting member 45. In the case where a transparent member such as a touch panel is disposed on the front face of the housing 2, the transmissive member 47 may be covered by the transparent member.

The second light source 46 is associated with medical information which is different from the information associated with the first light sources 42. For example, the second light source 46 may light up or blink in order to provide alarm information which is different from the alarm information that is provided by the light emission of the first light sources 42. Alternatively, the second light source 46 may light up or blink in order to provide medical information which is not alarm information.

According to the above configuration, a wider variety of information can be provided by using a part of the configurations of the alarm indicators 4 while suppressing the enlargement of the structure.

In the example illustrated in (C) of FIG. 1, only the alarm indicator 4 which is disposed in the upper portion of the housing 2 comprises the second light source 46 and the transmissive member 47. Additionally or alternatively, each of the alarm indicators 4 which are disposed in the right-side and left-side of the housing 2 may comprise the second light source 46 and the transmissive member 47. In this case, even when the direction of the monitor device 1 is changed in the right or left direction, a wide variety of information can be easily provided.

As illustrated in FIG. 2, the transmissive member 43 has a thin flat appearance. In this case, as illustrated in (C) of FIG. 1, the outer faces 43a of the transmissive members 43 of the alarm indicators 4 do not protrude from the respective side faces of the housing 2 which surround the information displaying section 3.

A conventional alarm indicator has a shape which remarkably protrudes from a side face of a housing because it is necessary to ensure optical paths that are oriented in various directions from the alarm indicator, thereby ensuring the visibility of light emitted from the alarm indicator. On the other hand, according to the above embodiment, light directed in various directions is obtained before the light passes through the transmissive member 43, with the aid of the light diffusion effect of the light guiding member 41. Therefore, the transmissive member 43 can be formed into a shape which is thin and flat enough to avoid protruding from the side face of the housing 2. This feature helps to avoid the enlargement of the structure.

The present application is based on Japanese Patent Application No. 2017-226970 filed on Nov. 27, 2017, the entire contents of which are hereby incorporated by reference.

The invention claimed is:

1. A medical display device comprising:
an information displaying section having a display screen in which medical information is displayed; and
an alarm indicator configured to provide alarm information,
wherein the alarm indicator comprises:
  a light guiding member extending in a first direction that is parallel to the display screen;
  a first light source facing an end face of the light guiding member in the first direction; and
  a transmissive member covering the light guiding member from a second direction intersecting with the first direction;
wherein the light guiding member comprises:
  a reflecting portion extending in the first direction and configured to reflect light incident from the end face at least toward the second direction; and
  an outer face configured such that the light reflected by the reflecting portion is emitted therefrom while being diffused.

2. The medical display device according to claim 1, wherein a section shape of the reflecting portion as seen in the first direction is the same as a section shape of the light guiding member as seen in the first direction.

3. The medical display device according to claim 1, wherein the outer face is formed with at least one of ridges and grooves extending in the first direction.

4. The medical display device according to claim 1, comprising:
a first reflecting member disposed between the first light source and the light guiding member,
wherein part of the light emitted from the first light source is reflected by the first reflecting member and is caused to be incident on the end face of the light guiding member.

5. The medical display device according to claim 1, comprising:
a second reflecting member configured to reflect light emitted from the outer face of the light guiding member toward the transmissive member.

6. The medical display device according to claim 1, comprising:
a second light source associated with medical information that is different from medical information associated with the first light source.

7. The medical display device according to claim 1, comprising:
a housing surrounding the information displaying section,
wherein an outer face of the transmissive member is not protruded from a side face of the housing.

8. The medical display device according to claim 1, comprising:
the first light source includes a pair of first light sources which face the end face and the other end face in the longitudinal direction of the light guiding member.

9. The medical display device according to claim 1, wherein the transmissive member is provided on a surface different than the display screen.

* * * * *